United States Patent [19]

Stein

[11] 4,116,046
[45] Sep. 26, 1978

[54] LIQUID CHROMATOGRAPHY SYSTEM

[75] Inventor: Stanley Stein, Bloomfield, N.J.

[73] Assignee: Hoffmann-La Roche Inc., Nutley, N.J.

[21] Appl. No.: 822,114

[22] Filed: Aug. 5, 1977

[51] Int. Cl.² .......................................... G01N 31/08
[52] U.S. Cl. ............................. 73/61.1 C; 210/198 C
[58] Field of Search ................. 73/61.1 C; 210/31 C, 210/198 C; 23/253 R

[56] References Cited

U.S. PATENT DOCUMENTS

| | | | |
|---|---|---|---|
| 3,373,872 | 3/1968 | Hrdina | 73/61.1 C X |
| 3,446,057 | 5/1969 | Bakalyar et al. | 73/61.1 C X |
| 3,518,874 | 7/1970 | Hrdina | 73/61.1 C |
| 3,536,450 | 10/1970 | Dus et al. | 73/61.1 C X |
| 3,559,458 | 2/1971 | Hrdina | 73/61.1 C X |
| 3,649,203 | 3/1972 | Schneider | 73/61.1 C X |
| 3,701,609 | 10/1972 | Bailey | 73/61.1 C X |
| 3,862,038 | 1/1975 | Takeuchi et al. | 210/198 C |

OTHER PUBLICATIONS

Dell'Ova, V. E., et al., *Ultrasonic Degasser for Use in Liquid Chromatography*, in Anat. Chem., 46(9): pp. 1365-1366, Aug. 1974.

*Primary Examiner*—Richard C. Queisser
*Assistant Examiner*—Joseph W. Roskos
*Attorney, Agent, or Firm*—Samuel L. Welt; Jon S. Saxe; George M. Gould

[57] ABSTRACT

A liquid chromatography system comprises the following major components in combination: gas pressurized buffer reservoirs, automatic buffer selection valve, mixer/debubbler chamber, pump means, automatic sample valve, chromatography column, detector and fraction collector.

5 Claims, 1 Drawing Figure

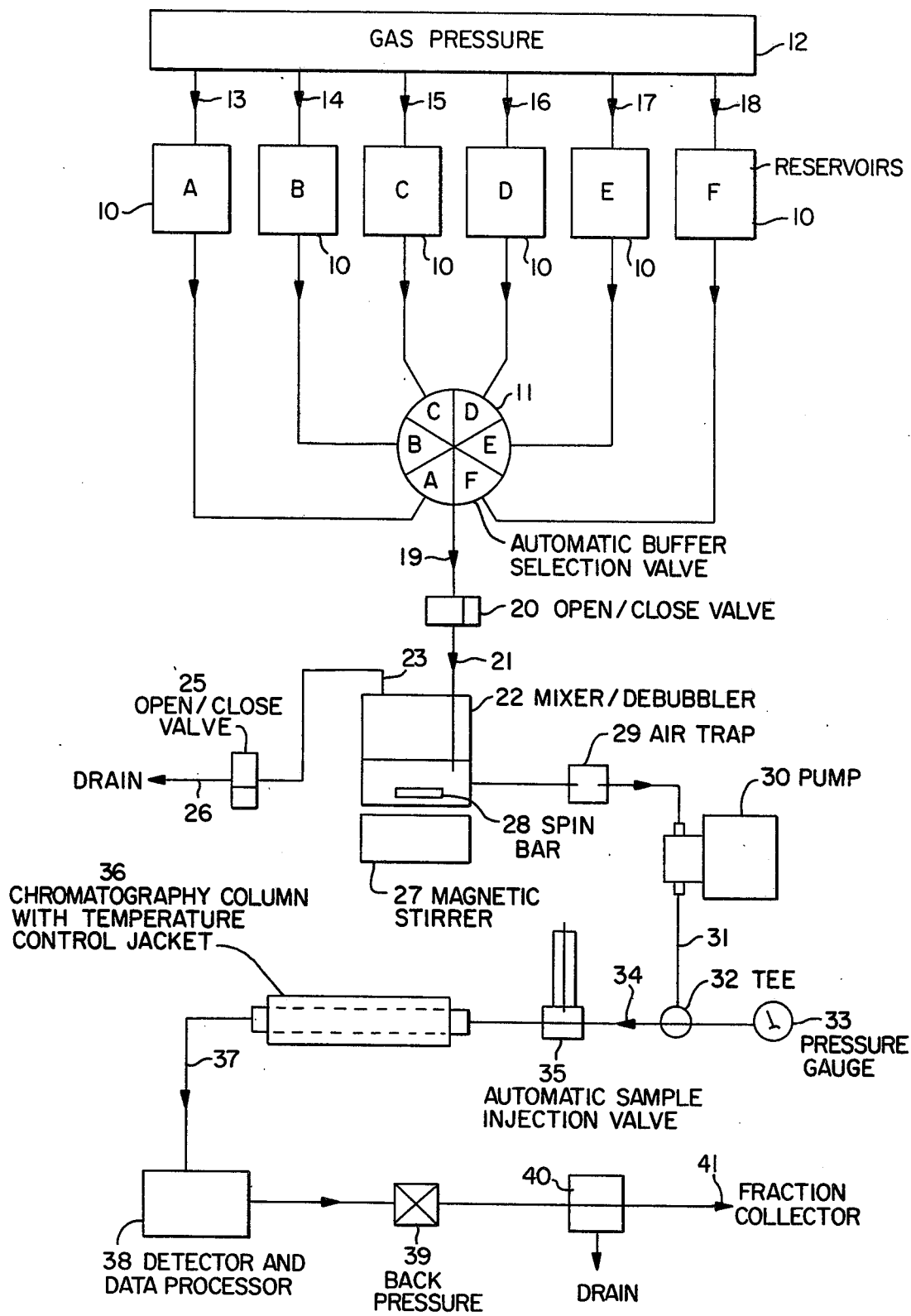

LIQUID CHROMATOGRAPHY SYSTEM

DESCRIPTION OF THE INVENTION

The present invention relates to a liquid chromatography system which is readily adapted for automatic operation.

The instant system is more readily understood by reference to the accompanying FIGURE which provides a schematic representation of the system.

In said FIGURE a number of buffer or solvent reservoirs 10 are provided and labeled A through F for convenient reference. The number of reservoirs is not narrowly critical and can vary from about 2 to 6. Each buffer reservoir may be pressurized utilizing pressurized gas derived from gas reservoir means 12 passing through gas inlet lines 13, 14, 15, 16, 17 and 18 respectively. The same system may be used without pressurizing the reservoirs. In this case the reservoirs would be placed at a certain height (e.g., 3 ft.) above the mixer/debubbler and gravity flow would then be in effect when valve 25 is opened.

The reservoirs can contain buffers or solvents which are conventionally employed in liquid chromatography systems. Examples of suitable buffers and solvents include pyridine-acetate, propanol-water, acetone-water and the like. The gas used for pressurization can be any inert gas which will not interact with the buffers or solvents used in the system or with the sample to be chromatographed.

Buffer or solvent flow to the system is controlled by a programmable, automatic buffer selection valve means 11 which is in operable fluid flow relationship with each of the aforesaid buffer reservoirs. The valve means 11 may be programmed to sequentially allow buffer flow from each of the said reservoirs for a desired pre-selected time period. The selected buffer then passes through line 19, on/off control valve means 20 and line 21 into a mixer-debubbler chamber 22. This chamber will generally have a volume in the range of from about 0.1 to 50 ml and performs several functions in the instant system. As a mixing chamber it forms a concentration gradient between the buffer just selected and the prior contents. Mixing in the chamber can be accomplished by means known in the art for this purpose. A preferred method for this purpose involves the use of a magnetic spin bar 28 inside the chamber which is activated by a magnetic stirrer 27 located directly below the chamber.

Stirring achieves not only the formation of a concentration gradient between successive buffers but also achieves debubbling by separation of entrapped gases in the liquid found in chamber 22. Gas which accumulates in this chamber is removed by opening valve 25 when valve 20 is also opened. The positive pressure on the system will drive off the accumulated gas through line 23 and out of the system via drain 26. Opening of valve 25 may also be utilized to remove liquid from chamber 22 via line 23 out through drain 26, so as to allow the most rapid introduction of the next buffer in the sequence.

Flow rate of the buffer leaving chamber 22 is controlled by means of a pump 30. If desired, an air trap 29 may be introduced upstream of the pump. The type of pump employed is not narrowly critical to the invention. However, should a pulsating type pump be employed it is highly desirable that a pulse dampening means be introduced downstream of the pump. A suitable pulse dampening means for this purpose is the introduction of pressure gauge 33 into line 34 by means of tee 32. This gauge also is used to monitor the pump discharge pressure.

A programmable, automatic sample injection valve 35 injects samples in a sequential fashion into the buffer stream carried by line 34. The sample containing fluid is then passed into a conventional chromatography column 36. The column may contain conventional liquid separation materials such as for example, ion-exchange or reverse-phase resins. To insure proper conditions for reproducible separations, the column may be provided with a temperature control jacket.

The column effluent containing separated components of said samples passes out through line 37 and is then introduced into the detection means 38 conventional detection devices may be employed to identify the presence of sample components such as for example a fluorometer and/or an absorptiometer. The detector means can also contain data reduction instrumentation to effect plotting of a chromatogram on a recorder and also may determine and record parameters such as peak elution time, peak height and peak area in a manner known per se.

To insure that no bubbling occurs in the flow cell of the detector it is useful to introduce back pressure means 39, preferably narrow bore tubing, downstream of the detector instrumentation.

The sample stream, after passing through the detector 38 can either be discharged from the system through claim 42 or can be collected by passage to fraction collector 41 by suitable adjustment of three-way valve 40 which can be programmed to all material in individual peaks to be collected. A typical programmed run would be as follows:

Sample No. 1 is injected into the column, Buffers A, B, C, D, E and F are pumped through the column sequentially for 5 minutes each. Column effluent between 18 and 23 minutes is collected in the fraction collector. Buffer A is then pumped through the column for 20 minutes in preparation for the next sample (re-equilibration). During this last 20 minute period any gas, as well as buffer F in the mixer/debubbler chamber is removed by opening the appropriate 2-way valve (valve 25). At the end of this time, sample number 2 is injected and the entire process is repeated. The fraction collector is advanced so that the effluent of sample number 2 between 18 and 23 minutes is collected in a fresh tube. When the last sample has been run, the pump, recorder, etc., are automatically shut off. The appropriate 2-way valve (valve 20) closes to prevent flow of solution from the reservoirs.

Run time for each sample is 6 × 5 min + 20 min = 50 min.

Ten runs would take 500 min.

I claim:

1. A fully automated liquid-column chromatography system comprising in combination:
   A. a plurality of gas pressurized buffer reservoir means;
   B. an automatic, programmable buffer selection valve means whereby controlled sequential buffer flow from said buffer reservoir means is obtained;
   C. mixer-debubbler, chamber means downstream of said buffer selection value means whereby a concentration gradient may be established between said buffers and said buffer stream is concomitantly debubbled;

D. pump means whereby the flow rate of said buffers is controlled;

E. automatic sample valve means downstream of said pump means whereby samples are injected into said buffer stream in a sequential manner;

F. liquid chromatography column means whereby components in said samples are separated and passed into a column effluent stream;

G. detection means for identifying the presence of said sample components in the column effluent stream; and H. fraction collection means.

2. The system of claim 1 wherein said mixer-debubbler chamber means contains a magnetic spin bar which is activated by a magnetic stirrer located directly below said chamber.

3. The system of claim 1 wherein said mixer-debubbler chamber means contains gas removal means and liquid removal means.

4. The system of claim 1 wherein said mixer-debubbler chamber has a volume in the range of from 0.1 to 50 ml.

5. The system of claim 1 wherein a pressure gauge is present downstream of said pump means.